United States Patent
Shimada et al.

(10) Patent No.: US 7,331,946 B2
(45) Date of Patent: Feb. 19, 2008

(54) DISPOSABLE PULL-ON UNDERGARMENT

(75) Inventors: Takaaki Shimada, Kagawa-ken (JP); Kenji Nakamura, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 333 days.

(21) Appl. No.: 09/976,182

(22) Filed: Oct. 11, 2001

(65) Prior Publication Data

US 2002/0045872 A1    Apr. 18, 2002

(30) Foreign Application Priority Data

Oct. 13, 2000  (JP)  .............................. 2000-314188

(51) Int. Cl.
 *A61F 13/15*  (2006.01)
(52) U.S. Cl. ................ 604/385.3; 604/385.29
(58) Field of Classification Search ...............
 604/385.24–385.3, 394, 396
See application file for complete search history.

(56) References Cited

U.S. PATENT DOCUMENTS 5,749,865 A * 5/1998 Yamamoto et al. .... 604/385.29
5,817,087 A * 10/1998 Takabayashi et al. .. 604/385.29
5,931,827 A * 8/1999 Buell et al. ............. 604/385.29
5,941,865 A * 8/1999 Otsubo et al. .......... 604/385.29
6,364,863 B1 * 4/2002 Yamamoto et al. .... 604/385.27

FOREIGN PATENT DOCUMENTS

| EP | 0 761 194 | 3/1997 |
| GB | 2 266 445 | 11/1993 |
| JP | 07-236650 | 9/1995 |

* cited by examiner

*Primary Examiner*—Tatyana Zalukaeva
*Assistant Examiner*—C. Lynne Anderson
(74) *Attorney, Agent, or Firm*—Butzel Long

(57) ABSTRACT

A disposable pull-on undergarment includes each of front and rear waist-encircling regions having a first elasticized zone and a second elasticized zone extending in a waist-encircling direction. Tensile stress of the first elasticized zone is greater than that of the second elasticized zone. The undergarment thus constituted can reduce an incidence of intense pressure locally exerted on a waist of a wearer of the undergarment and avoid an occasion whereby an excrement-absorbing function of a core is hindered.

4 Claims, 7 Drawing Sheets

DISPOSABLE PULL-ON UNDERGARMENT

BACKGROUND OF THE INVENTION

This invention relates to a disposable pull-on undergarment which absorbs and retains excrements.

Japanese Patent Application Publication No. 1995-236650A discloses a disposable pull-on diaper which comprises a liquid pervious top sheet, a liquid impervious back sheet and an liquid absorbent core interposed between those two sheets, with respective longitudinal side edges of front and rear waist-encircling regions being secured to each other to provide a waist-encircling opening and a pair of leg-encircling openings. In the front waist-encircling region, a plurality of waist elastic members are secured in an extended condition to an edge portion of the waist-encircling opening to extend in a waist-encircling direction. In an edge portion of each leg-encircling opening, a plurality of leg elastic members are secured in an extended condition to extend in a leg-encircling direction. Also, a plurality of auxiliary elastic members are secured in a location intermediate between the waist elastic members and the leg-encircling opening edge portions to extend in the waist-encircling direction between the longitudinal side edges of the front and rear waist regions.

Each auxiliary elastic member has an extensible portion and a non-extensible portion. The extensible portion extends from longitudinal side edges of the core positioned over the front and rear waist-encircling regions toward respective longitudinal side edges of the front waist-encircling region. The non-extensible portion traverses the core to extend between opposite longitudinal side edges of the core. The extensible portions of the auxiliary elastic members act to squeeze a wearer's waist so that the diaper while in use is prevented from sliding down from its position. In the non-extensible portions of the auxiliary elastic members, the diaper is not subjected to an extension stress from the auxiliary elastic members which may otherwise cause the core to contract, so that the core is prevented from puckering.

The diaper disclosed in the above-identified reference relies solely on the extensible portions of auxiliary elastic members to prevent its downward slide and accordingly needs to increase an extension stress of the auxiliary elastic members in their extensible portions. Such a diaper thus squeezes a wearer's waist in a severe manner and provides discomfort to a wearer of the diaper. The non-extensible portions of auxiliary elastic members do not act to press the core against a wearer's skin. This increase a tendency of the core to be spaced away from the wearer's skin during the use of the diaper, and accordingly hinders an excrement-absorbing function of the core.

SUMMARY OF THE INVENTION

It is an object of this invention to provide a disposable pull-on undergarment which can reduce an incidence of local exertion of an intense pressure on a waist of a wearer of the garment and can avoid an incidence whereby an excrement-absorbing function of the core is hindered.

According to the present invention, there is provided a disposable pull-on undergarment which comprises a liquid pervious top sheet, a liquid impervious back sheet and an liquid absorbent core interposed between the top and back sheets and includes front and rear waist encircling regions opposed to each other, a crotch region positioned between the front and rear waist-encircling regions, and a waist-encircling opening and a pair of leg-encircling openings defined by joining respective longitudinal sides edges of the front and rear waist-encircling regions, with at least one of the front and rear waist-encircling region is being rendered elastically contractible in a waist-encircling direction.

The disposable pull-on undergarment further comprises each of the front and rear waist-encircling regions has a first elasticized zone which extends in the waist-encircling direction from opposite longitudinal side edges of the region to the vicinities of opposite side edges of the core, and a second elasticized zone which traverse the core to extend in the waist-encircling direction between the vicinities of opposite side edges of the core, and tensile stress of the first elasticized zone being greater than that of the second elasticized zone.

In accordance with one exemplary embodiment of the present invention, the waist elastic members extending in the waist-encircling direction are attached in an extended condition to an edge portion of the waist-encircling opening. A plurality of auxiliary elastic members spaced longitudinally apart from each other by a specific distance and extending in the waist-encircling direction in the first and second elasticized zones are attached in an extended condition to a location between the waist elastic members and the edge portions of the leg-encircling openings. The extension stress of the auxiliary elastic members is greater in the first elasticized zone than in the second elasticized zone.

In accordance with another exemplary embodiment of the present invention, the waist elastic members extending in the waist-encircling direction are attached in an extended condition to an edge portion of the waist-encircling opening. A plurality of first auxiliary elastic members spaced longitudinally from each other by a specific distance and extending in the waist-encircling direction in the first and second elasticized zones are attached in an extended condition to a location intermediate between the waist elastic members and the edge portions of the leg-encircling openings. A plurality of second auxiliary elastic members spaced longitudinally from each other by a specific distance and extending in the waist-encircling direction in the first elasticized zone are attached in an extended condition to a location intermediate between the waist elastic members and the edge portions of the leg-encircling openings. Tensile stress of the first auxiliary elastic members is smaller than or equal to that of the second auxiliary elastic members.

In a further exemplary embodiment of the present invention, the first elasticized zone when extended to a maximum extent exhibits an extension stress in a range of 0.2-2.0 N/25 mm and the second elasticized zone when extended to a maximum extent exhibits an extension stress in a range of 0.1-0.6 N/25 mm.

DETAILED DESCRIPTION OF THE PREFERRED EMBODIMENTS

A disposable pull-on undergarment in accordance with the present invention is below described in detail with reference to the attached drawings as it is used in a disposable pull-on diaper.

Figure 1:
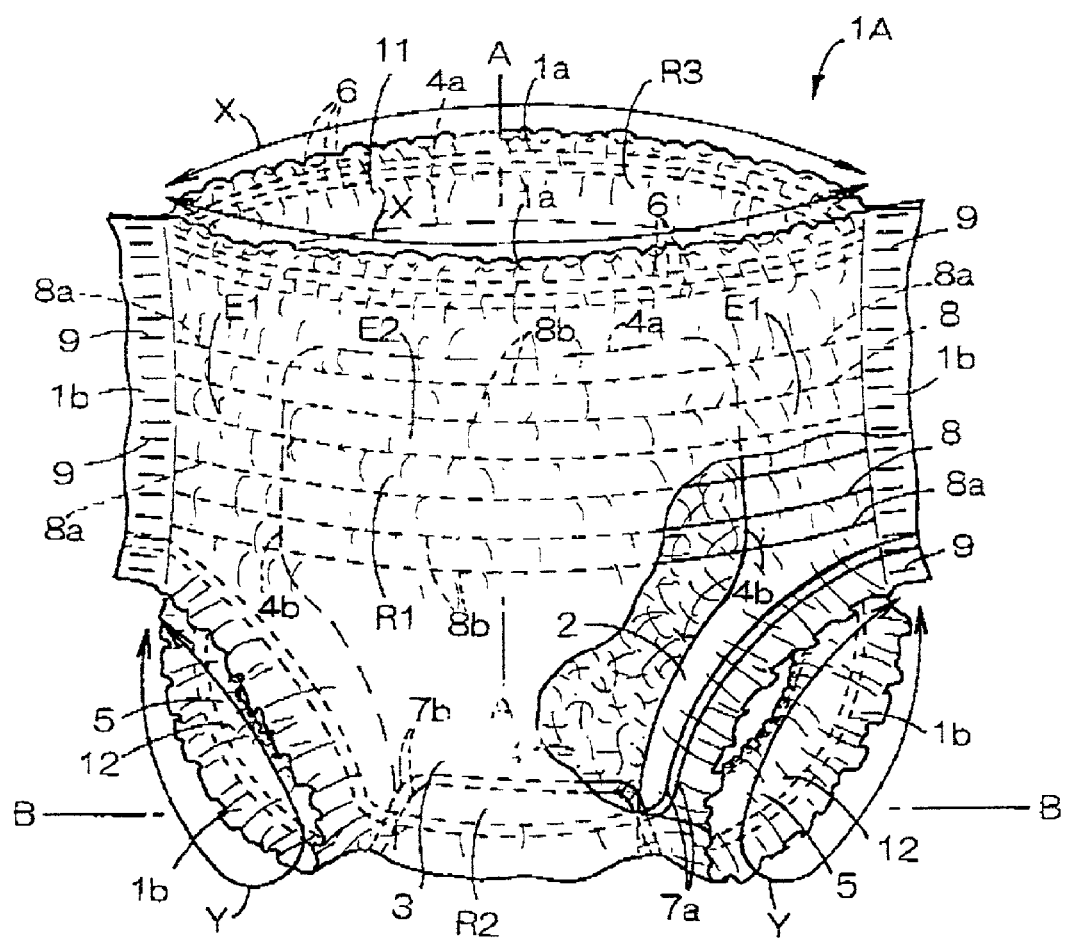
FIG. 1 is a partially cut-away perspective view of a disposable diaper as one exemplary undergarment.
Figure 2:
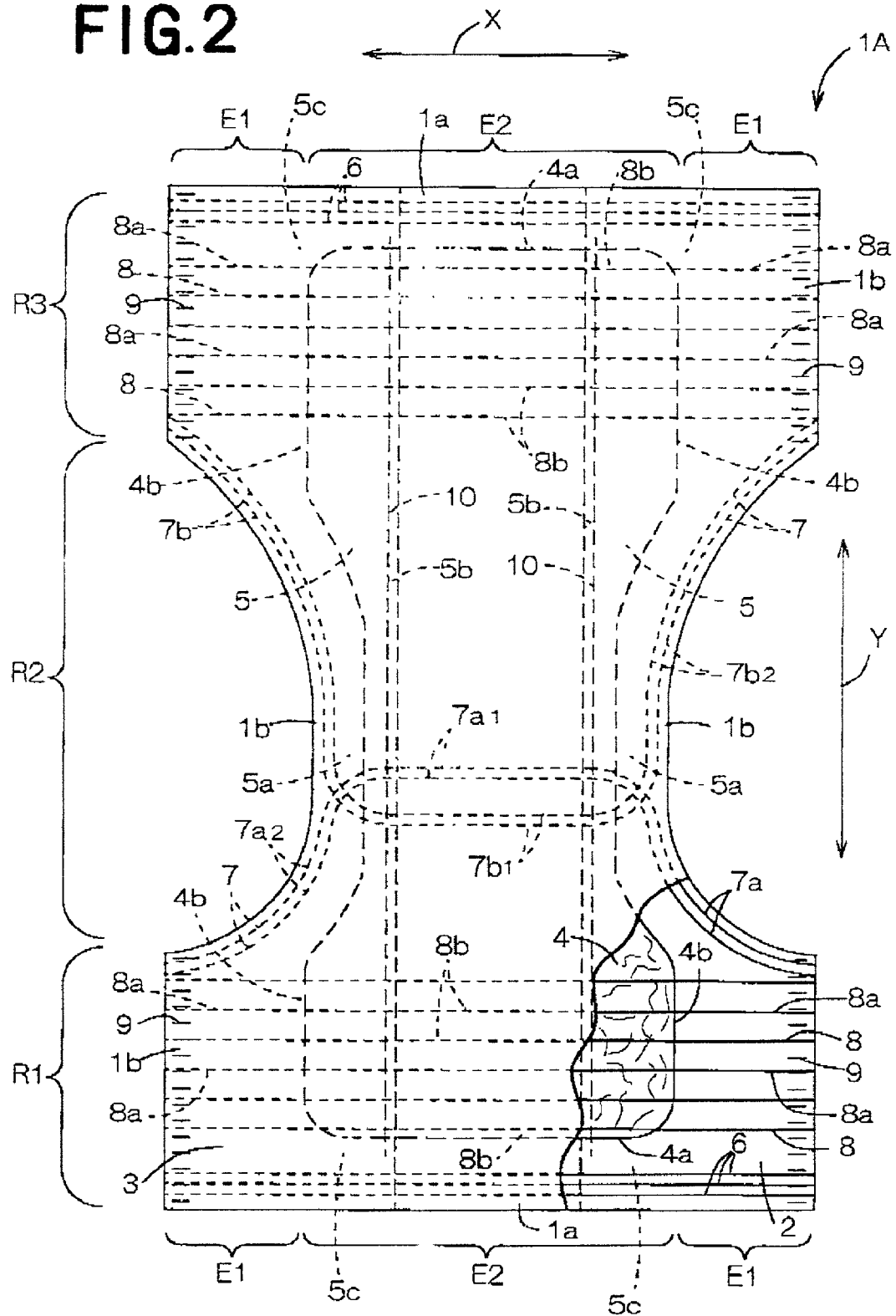
FIG. 2 is a partially cut-away plan view of the diaper when the front and rear waist regions are disconnected from each other and developed longitudinally.

FIG. 1 is a partially cut-away perspective view of a disposable diaper 1A. FIG. 2 is a partially cut-away plan view of the diaper 1A when its front and rear waist-encircling regions R1, R3 are disconnected from each other and developed in a longitudinal direction. In FIG. 1, a waist-encircling direction is shown by the arrow X and a leg-encircling direction is shown by the arrow Y. In FIG. 2, the diaper 1A is viewed from a side of its back sheet 3. A lateral direction and a longitudinal direction are shown by the arrows X and Y, respectively. An inside surface of the top or back sheet 2, 3 means its surface positioned to face toward a core 4. An outside surface of the top or back sheet 2, 3 means its surface positioned away from the core 4.

The diaper 1A primarily comprises a liquid pervious top sheet 2, a liquid impervious back sheet 3, a liquid-absorbing core 4 interposed between the top and back sheets 2, 3 and enveloped entirely by and joined to a liquid-diffusion sheet such as tissue paper (not shown) and a substantially liquid impervious, leakage-resistant cuff 5. The core 4 is joined via the liquid-diffusion sheet to inside surfaces of the top and back sheets 2 and 3.

The diaper 1A includes front and rear waist-encircling regions R1 and R3 opposed to each other, and a crotch region R2 positioned intermediate between the front and rear waist-encircling regions R1, R3. A waist-encircling opening 11 and a pair of leg-encircling openings 12 are defined in the diaper 1A.

As shown in FIG. 2, the diaper 1A has laterally-extending end edges 1a and longitudinally-extending side edges 1b. The side edges 1b in the crotch region R2 each describes a curve toward a laterally inward direction of the diaper 1A.

A plurality of laterally extending waist elastic members 6 are secured in an extended condition along each end edge 1a. In the crotch region R2, a plurality of leg elastic members 7 are secured in an extended condition along each side edge 1b. In each of the front and rear waist-encircling regions R1 and R3, a plurality of auxiliary elastic members 8 extending laterally and spaced longitudinally apart from each other by a specific distance are secured in an extended condition in a location intermediate between the waist and leg elastic members 6 and 7.

The diaper 1A is formed into a pull-on type by bringing opposite side edge 1b located respectively in the front and rear waist-encircling regions R1 and R3 into flat contact with each other and securing them to each other at plural joints 9 arranged in an intermittent manner along the longitudinal direction.

In the diaper 1A, the end edges 1a define an edge portion 1a of the waist-encircling opening 11, and the side edges 1b define respective edge portions 1b of the leg-encircling openings 12 in the crotch region R2, as shown in FIG. 1. The waist elastic members 6 extend in the waist-encircling direction in the edge portion 1a of the waist-encircling opening 11. The leg elastic members 7 extend in the leg-encircling direction along the edge portion of each leg-encircling opening 11. The auxiliary elastic members 8 extend in the waist-encircling direction in an area located intermediate between the waist elastic members 6 and the leg-encircling opening edge 1b.

The front and rear waist-encircling regions R1, R3 of the diaper 1A each has a first elasticized zone E1 and a second elasticized zone E2. In each of the front and rear waist-encircling regions R1 and R3, the first elasticized zone E1 extends in the waist-encircling direction from opposite side edges 1b to the vicinities of opposite side edges 4b of the core 4. The second elasticized zone E2 traverses the core to extend in the waist-encircling direction between the vicinities of opposite side edges 4b of the core 4. The auxiliary elastic members 8 exhibit a higher extension stress in their portions 8a that extend in the first elasticized zone E1 than in their portions 8b that extend in the second elasticized zone E2. Hence, in the diaper 1A, the first elasticized zone E1 is related to the second elasticized zone E2 by extension stress as first elasticized zone E1>second elasticized zone E2.

In the diaper 1A, the first elasticized zone E1 when extended to a maximum extent exhibits an extension stress in the range of 0.2-2.0 N/25 mm, preferably in the range of 0.4-1.0 N/25 mm. The second elasticized zone E2 when extended to a maximum extent exhibits an extension stress in the range of 0.1-0.6 N/25 mm.

The following procedure is utilized to measure extension stress for the first and second elasticized zones E1 and E2. (1) First, the first elasticized zone E1 is partially cut out to provide a first test piece and the second elasticized zone E2 is partially cut out to provide a second test piece. The first test piece includes portions 8a of the auxiliary elastic members 8, and has a dimension of 100 mm in the waist-encircling direction and a dimension of 25 mm in the longitudinal direction. The second test piece includes portions 8b of the auxiliary elastic members 8 (excluding the core 4), and has a dimension of 100 mm in the waist-encircling direction and a dimension of 25 mm in the longitudinal direction. (2) Then, the extension stress of each test piece is measured using a tensile tester. In the measurement of extension stress, each test piece once allowed to contract by relief from tension is again extended by the tensile tester to a size of 100 mm. The extension stress is a value measured when each test piece is extended to a maximum size of 100 mm.

In the diaper 1A, the first elasticized zone E1 exhibits a higher extension stress than the second elasticized zone E2. Accordingly, when the diaper is worn, the first elasticized zone E1 squeezes a wearer's waist more tightly than the second elasticized zone E2. However, in accordance with the diaper 1A, the first elasticized zone E1 is not the only one that acts on the wearer but acts in concert with the second elasticized zone E2 to squeeze the wearer's waist in such a way as to prevent the diaper 1A from sliding down from its position. Thus, the extension stress of the first elasticized zone E1 in this diaper is not required to be increased to the level required for the prior art diaper construction and can be maintained within the above-specified range.

In the second elasticized zone E2 in the diaper 1A, the portions 8b of the auxiliary elastic members 8 press the core 4 against the wearer's skin by their extension stress so that the core 4 of the diaper 1A while in use is prevented from being spaced apart from the wearer's skin. As a result, the occasion where the excrement-absorbing function of the core 4 is hindered can be avoided. Since the extension stress of the second elasticized zone E2 in the diaper 1A is maintained within the above-specified range, the core 4, because of its rigidity, withstands the force exerted by the second elasticized zone E2 when contracted and is thus prevented from puckering.

If the extension stress of the first elasticized zone E1 is below 0.2 N/25 mm, the compression of the first elasticized zone E1 around the wearer's waist becomes weak to result in the increased tendency of the diaper 1A to slide down from its position. If the extension stress of the first elasticized zone E1 exceeds 2.0 N/25 mm, the compression of the first elasticized zone E1 around the wearer's waist becomes excessively strong. The resulting intense pressure on the wearer's waist provides discomfort to the wearer of the diaper 1A. It the extension stress of the second elasticized zone E2 is below 0.1 N/25 mm, it may fail to press the core 4 against the wearer's skin to result in some occasions where the core 4 is spaced apart from the wearer's skin. If the extension stress of the second elasticized zone E2 exceeds 0.6 N/25 mm, the core 4 may be caused to pucker when the second elasticized zone E2 contracts to result in some occasions where the core 4 is spaced apart from the wearer's skin.

The leakage-resistant cuff 5 extends longitudinally along each side edge 1b of the diaper 1A. Each cuff 5 has a fixed edge 5a that extends longitudinally adjacent the side edge 4b of the core 4, a free edge 5b that is associated with the fixed edge 5a and biased to be spaced apart from the top sheet 2, fixed ends 5c each folded laterally inwardly to overlie the top sheet 2, and side portion 5d (refer to FIG. 4) that extends from the fixed side edge 5a toward the side edge 1b of the diaper 1A. An elastic member 10 is attached in an extended condition to the free edge 5b. The elastic member 10 is enclosed in a sleeve portion defined in the free edge 5b.

The leg-encircling elastic members 7 include a first leg elastic member 7a and a second leg elastic member 7b. These leg elastic members 7a and 7b each includes a central portion $7a_1$, $7b_1$ that traverses the crotch region R2 and opposite side portions $7a_2$, $7b_2$ that extend along the respective side edges 1b of the diaper, Each side portion $7a_2$ of the first leg elastic member 7a is located in about a front half of the side edge 1b portion that extends in the crotch region R2. Each side portion $7b_2$ of the second leg elastic member 7b is located in about a rear half of the side edge 1b portion that extends in the crotch region R2.

Figure 3:
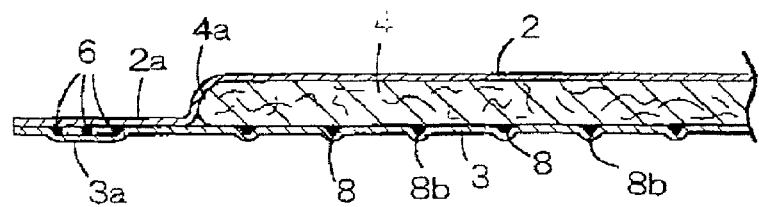
FIG. 3 is an end view taken along the line A-A of FIG. 1.
Figure 4:
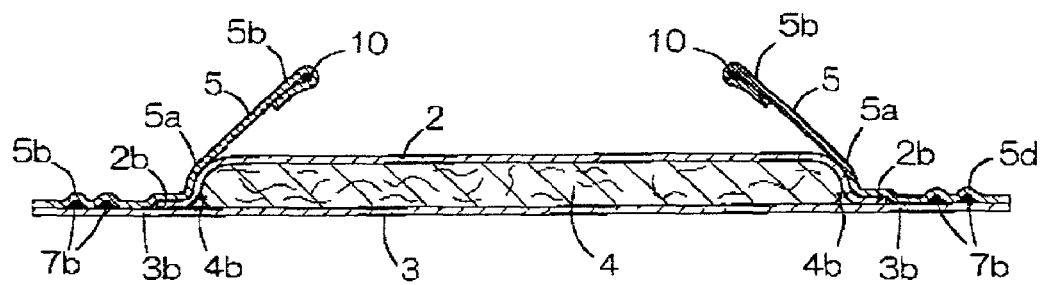
FIG. 4 is an end view taken along the line B-B of FIG. 1.

FIGS. 3 and 4 are views taken along the line A-A and the line B-B, respectively. In each side edge 1a of the diaper 1A, an end 2a of the top sheet 2 and an end 3a of the backsheet 3 extend together outwardly from the side edge 4a of the core 4 where inward surfaces of those ends 2a, 3a are joined to each other, as shown in FIG. 3. The waist elastic members 6 and the portions 8a of the auxiliary elastic members 8 are interposed between the top sheet 2 and the back sheet 3 and joined to their respective inward surfaces by mean of adhesives (not shown). The portions 8b of the auxiliary elastic members 8 are interposed between the backsheet 3 and the core 4 and joined to the inward surface of the back sheet 3 by mean of adhesives (not shown).

In each side edge portions 1b of the diaper 1A, the side portion 2b of the top sheet 2 is positioned between a side portion 3b of the back sheet 3 and a side portion 5d of the cuff 5 and secured to those portions 3b, 5d, as shown in FIG. 4. The side portions 3b, 5d are secured to each other where they overlap. When the elastic member 10 contracts, the free edge 5b of the cuff 5 is caused to stand up away from the top sheet 2 to form a barrier against excrements. The leg elastic members 7 are positioned between the side portion 3b of the back sheet 3 and the side portion 5d of the and secured to those side portions 3b, 5d by means of adhesives (not shown).

Figure 5:
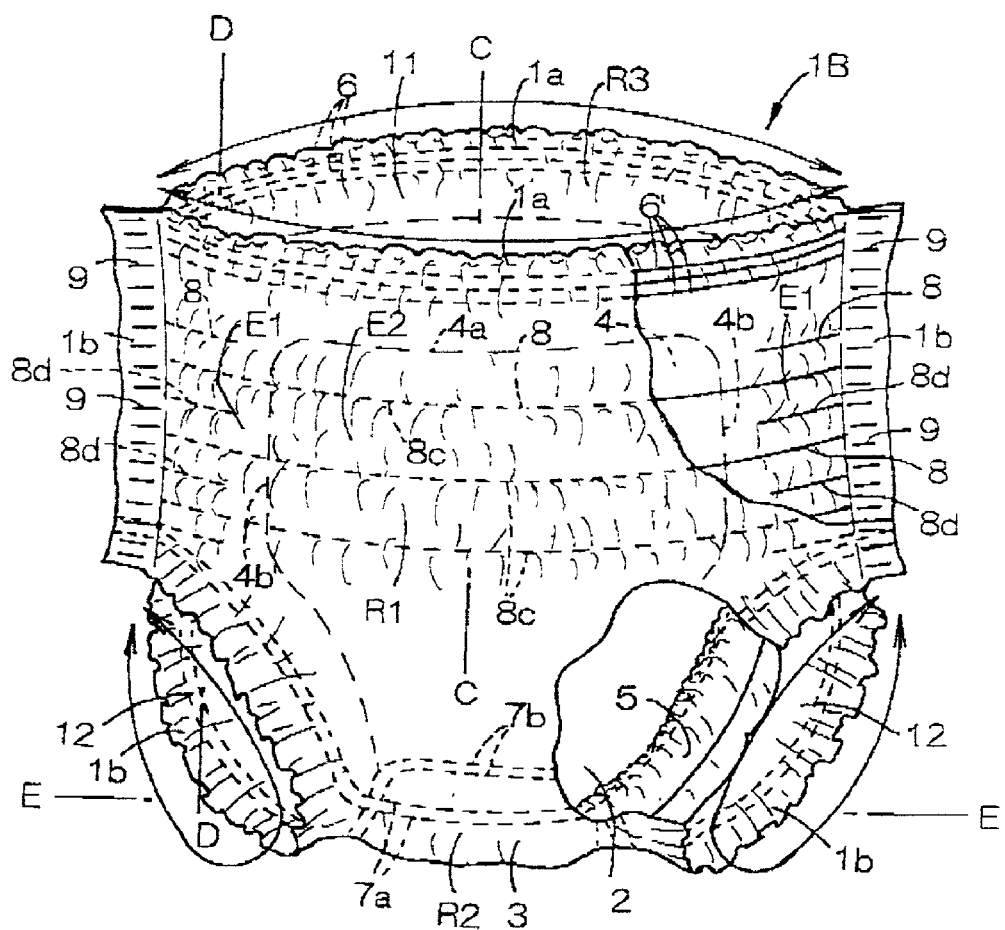
FIG. 5 is a partially cut-away perspective view of a disposable diaper as another exemplary undergarment.
Figure 6:
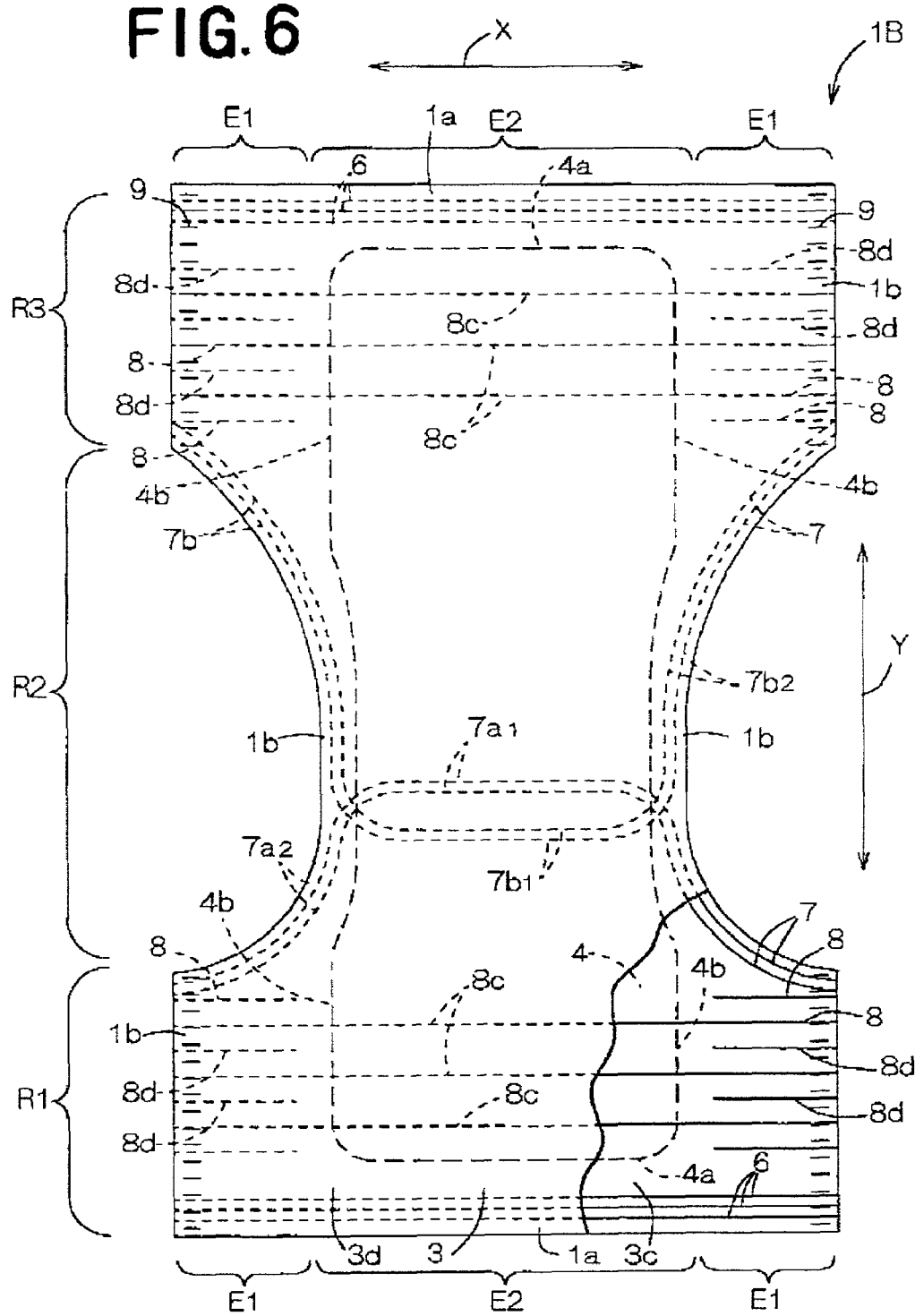
FIG. 6 is a partially cut-away plan view of the diaper when the front and rear waist regions are disconnected from each other and developed longitudinally.
Figure 7:
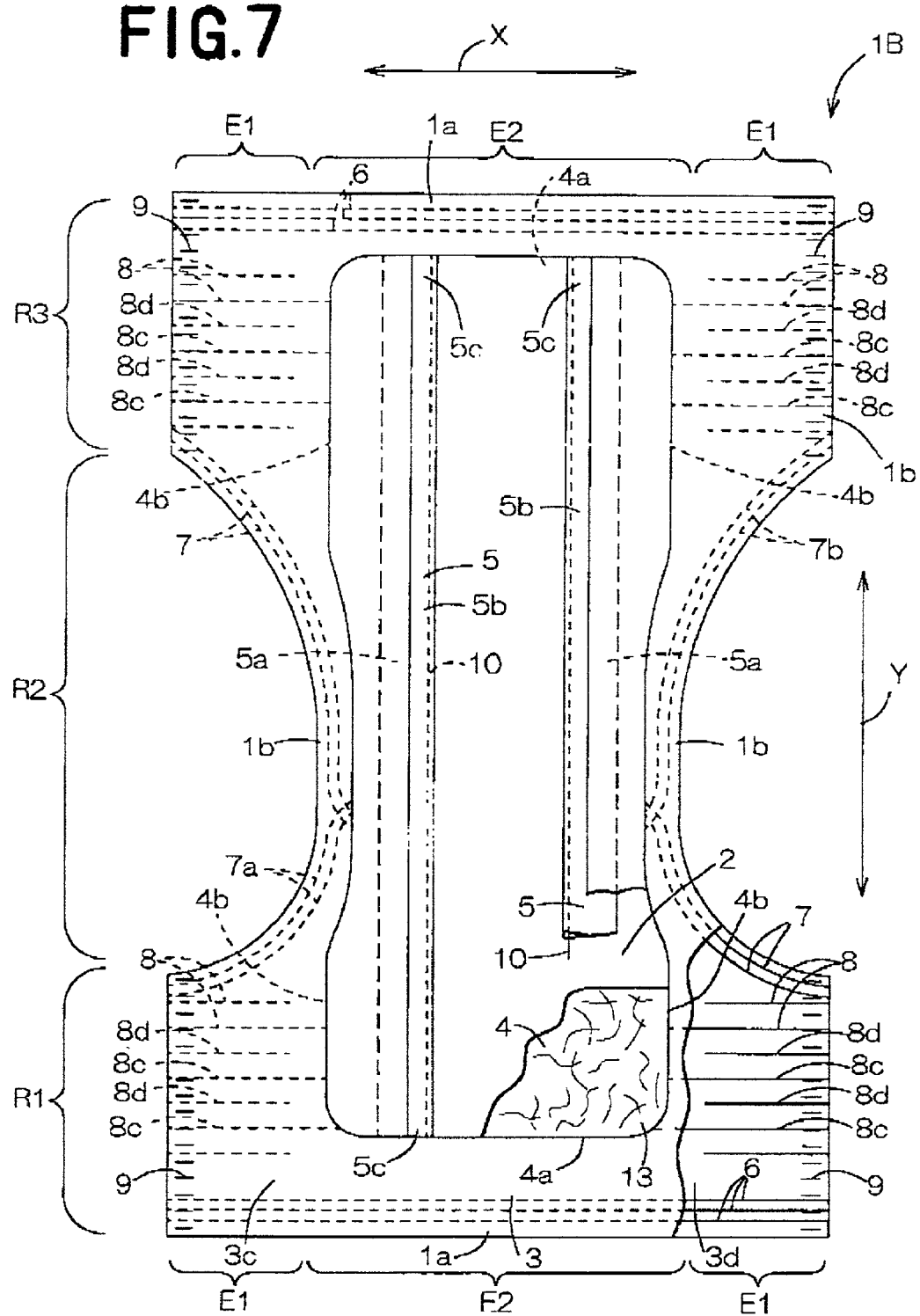
FIG. 7 is a view similar to FIG. 6 but viewed from a side of the top sheet.

FIG. 5 is a partially cut-away perspective view of a diaper 1B in accordance with another exemplary embodiment. FIG. 6 is a partially cut-away plan view of the diaper 1B when its front and rear waist-encircling regions R1, R3 are disconnected from each other and developed in a longitudinal direction FIG. 7 is similar to FIG. 6 but viewed from a side of the top sheet 2. In FIG. 5, a waist-encircling direction and a leg-encircling direction are indicated by the arrows X and Y, respectively. In FIGS. 6 and 7, a lateral direction and a longitudinal direction are indicated by the arrows X and Y, respectively.

The diaper in shown in FIG. 5 differs from the diaper shown in FIG. 1 in the following respects. In the diaper 1B, a liquid impervious back sheet 3 is first formed into a pull-up type, and a liquid-absorbing core 4 covered with a liquid pervious top sheet 2 and a waterproof film 13 is secured to an inward surface of the back sheet 3. The core 4 is enclosed entirely by and joined to a tissue paper (not shown). The core 4 is joined via the tissue paper to the inside surfaces of the top sheet 2 and the waterproof film 13.

As shown in FIG. 6, the diaper 1B has opposite end edges 1a and opposite side edges 1b. The side edges 1b in the crotch region R2 each describes a curve toward a laterally inward direction of the diaper 1B. In each of the front and rear waist-encircling regions R1 and R3, a plurality of the auxiliary elastic members 8 extending laterally and spaced longitudinally apart from each other by a specific distance are secured in an extended condition in a location intermediate between the waist elastic members 6 and the leg elastic members 7A or 7B. The auxiliary elastic members 8 include a plurality of first auxiliary elastic members 8c and a plurality of second auxiliary elastic members 8d.

As shown in FIG. 5, the first auxiliary elastic members 8c are spaced longitudinally from each other by a specific distance and extend in a waist-encircling direction in a first elasticized zone E1 and a second elasticized zone E2. The second auxiliary elastic members 8d are spaced longitudinally apart from each other by a specific distance and extend in a waist-encircling direction in the first elasticized zone E1. The first and second auxiliary elastic members 8c and 8d are related to each other by extension stress as first auxiliary elastic member 8c≦second auxiliary elastic member 8d.

In the diaper 1B, even in the case where the extension stress of the first auxiliary elastic member 8c is comparable to that of the second auxiliary elastic member 8d, the first elasticized zone E1 in which the first and second auxiliary elastic members 8c, 8d extend shows a higher extension stress compared to the second elasticized zone E2 in which only the first auxiliary elastic member 8c extend. Hence, in the diaper 1B, the first and second elasticized zones E1 and E2 are related to each other by extension stress as first elasticized zone E1>second elasticized zone E2.

In the diaper 1B, the first elasticized zone E1 when extended to a maximum extent exhibits an extension stress in the range of 0.2-2.0 N/25 mm, preferably in the range of 0.4-1.0 N/25 mm, and the second elasticized zone E2 when extended to a maximum extent exhibits an extension stress in the range of 0.1-0.6 N/25 mm. The extension stress of the first auxiliary elastic member may be adjusted higher in the elasticized zone E1 than in the second elasticized zone E2.

The extension stresses of those elasticized zones E1 and E2 are measured according to the same procedure as applied to the diaper 1A shown in FIG. 1 in the measurement, the first test piece includes the first auxiliary elastic members 8c and the second test piece further includes the second auxiliary elastic members 8*d* (excluding the core 4).

The diaper 1B when worn squeezes a wearer's waist more tightly in the first elasticized zone E1 than in the second elasticized zone E2. However, the first and second elasticized zones E1 and E2 act in connection with each other to hold the diaper 1B around the wearer's waist and prevent the diaper 1B from sliding down from its position. This permits the extension stress of the first elasticized zone E1 to remain within the above-specified range.

In the second elasticized zone E2 of the diaper 1B, the core 4 is pressed against the wearer's skin by the extension stress of the first auxiliary elastic members 8*c* so that its excrement-absorbing function is not hindered. Since the extension stress of the second elasticized zone E2 in the diaper 1B is maintained within the above-specified range, the core 4, because of its rigidity, withstands the force exerted by the second elasticized zone E2 when contracted and is thus prevented from puckering.

Figure 8:
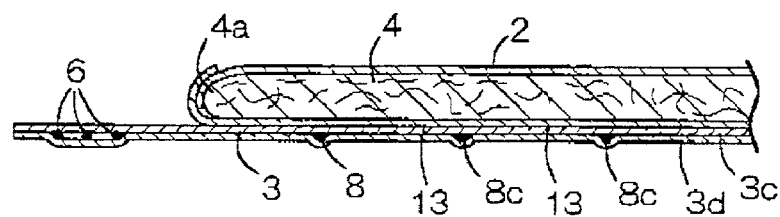
FIG. 8 is an end view taken along the line C-C of FIG. 5.
Figure 9:
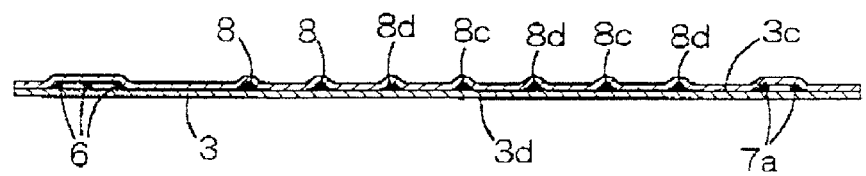
FIG. 9 is an end view taken along the line D-D of FIG. 5.
Figure 10:
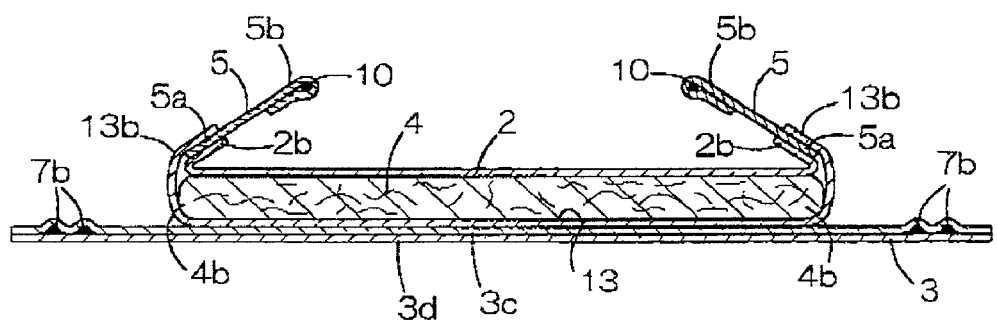
FIG. 10 is an end view taken along the line E-E of FIG. 5.

FIGS. 8 and 9 are end views taken along the line C-C and the line D-D of FIG. 5, respectively. FIG. 10 is an end view taken along the line E-E of FIG. 5. A back sheet 3 comprises two superimposed hydrophobic non-woven fabrics 3*c* and 3*d*, with those non-woven fabrics 3*c*, 3*d* being joined to each other at their opposing surfaces in an intermittent manner. The back sheet 3 may comprise a composite sheet made by laminating a hydrophobic non-wove fabric and a plastic film.

Waist elastic members 8 first and second leg elastic members 7*a* and 7*b*, and first and second auxiliary elastic members 8*c* and 8*d* are all positioned between the non-woven fabrics 3*c* and 3*d* together constituting the back sheet 3 and secured to those non-woven fabrics 3*c*, 3*d* by adhesives (not shown).

In the diaper 1B, a side portion 2*b* of the top sheet 2 and a side portion 13*b* of a waterproof film 13 extend outwardly from each side edge 4*b* of the core 4, as shown in FIG. 10. The film side portion 13*b* is folded upwardly from each side edge 4*b* of the core 4 to overlie an outside surface of the top sheet 2. The fixed edge 5*a* of the leakage-resistant cuff 5 is located between and secured to the side portions 2*b* and 13*b*. The fixed ends 5*c* of the cuff 5 are both secured to the outside surface of the top sheet 2. The free edge 5*b* of the cuff 5 is caused to stand up away from the top sheet 2 by contraction of the elastic member 10.

Non-woven fabrics of hydrophilic fibers and porous plastic films can be used for the top sheet 2. Non-woven fabrics of hydrophilic fibers, liquid impervious plastic films and laminate sheets comprised of a hydrophilic non-woven fabric and a liquid impervious plastic film can be used for the back sheet 3 of the diaper 1A shown in FIG. 1. Non-woven fabrics of hydrophilic fibers can be used for the leakage-resistance cuff 5. Flexible plastic films can be used for the waterproof film 13.

A composite non-woven fabric made by interposing a highly water-resistant melt-blown non-woven fabric between high-strength and high-flexibility spun-bonded non-woven fabrics can also be used for the back sheet 3, 3*c*, 3*d* and the cuff 5 of the shown diaper embodiment 1A, 1B.

Useful non-woven fabrics can be manufactured by various techniques including spun-lacing, needle punching, melt blown, thermal bonding, spun-bonding, chemical bonding, air-through and other processes. Examples of useful fibers constituting such non-woven fabrics include fibers such as of polyolefin, polyester and polyamide, sheath-core and side-by-side conjugate fibers such as of polyethylene/polypropylene or polyester.

The elastic members 6, 7, 8 and 10 comprise an elastomer such as of a natural or synthetic rubber. In the shown diapers 1A, 1B, elastic strands are used for the elastic members 6, 7, 8 and 10. However, elastic bands are also useful for the elastic members 6, 7, 8 and 10.

In the shown diaper embodiments 1A and 1B, the elastic members 6, 7, 8 and 10 may be secured, either in an intermittent or continuous manner, to the top and back sheets 2, 3, 3*c*, 3*d* and the cuff 5 by means of adhesives. Also in the shown diaper embodiments 1A and 1B, the waist elastic members 6 and the auxiliary elastic members 8 may be attached to at least one of the front and rear waist-encircling regions R1 and R3.

The core 4 comprises a mixture of fluff pulps, high-absorbent polymer particles and thermoplastic synthetic fibers and is provided in the form of being compressed to a specific thickness. Accordingly, the core 4 exhibits higher rigidity compared to the top and back sheets 2, 3, 3*c*, 3*d* and the cuff 5. Examples of useful high-absorbent polymers include starch-, cellulose- and synthetic polymer-based polymers.

Hot-melt adhesives or welding means such as sonic sealing or heat sealing can be utilized to secure the top sheet 2 to the hack sheet 3, 3*c*, 3*d*, secure the leakage-resistant cuff 5 and waterproof film 13, and join the core 4.

The disposable pull-up undergarment in accordance with the present invention, when worn by a wearer, squeezes the wearer's waist by the extension stress of the first and second elasticized zones so that the undergarment while being worn can be prevented from sliding down from its position. The following relationship exists in the undergarment; first elasticized zone>second elasticized zone, in terms of extension stress. Accordingly, the undergarment when worn squeeze a wearer's waist more tightly in the first elasticized zone than in the second elasticized zone. However, the first and second elasticized zones act in concert with each other to hold the undergarment around the wearer's waist. Hence, the extension stress of the first elasticized zone in this undergarment is not required to be increased to the level required for the prior art garment construction. As a result, the occasion can be avoided where the first elasticized zone exerts a strong pressure on the wearer's waist.

In accordance with the undergarment, the core is pressed against the wearer's skin by the extension stress of the second elasticized zone so that it is prevented from being spaced apart from the wearer's skin. As a result, the occasion whereby the excrement-absorbing function of the core is hindered can be avoided. Also in accordance with the undergarment, the core, because of its rigidity, withstands the force exerted by the second elasticized zone when it contracts and is thus prevented from puckering. As a result the occasion whereby the core is spaced apart from the wearer's skin can be avoided.

What is claimed is:

1. A disposable pull-on undergarment which comprises:
   a liquid pervious top sheet;
   a liquid impervious back sheet;
   a liquid absorbent core interposed between the top and back sheets;
   front and rear waist-encircling regions opposed to each other and having longitudinal side edges that are joined together, at least one of said front and rear waist-encircling regions being elastically contractible in a waist-encircling direction;
   a crotch region positioned between the front and rear waist-encircling regions;

a waist-encircling opening;

a pair of leg-encircling openings;

waist elastic members extending in the waist-encircling direction are attached in an extended condition to an edge portion of the waist-encircling opening; and a plurality of auxiliary elastic members spaced longitudinally apart from each other and extending in the waist-encircling direction in the first and second elasticized zones, said plurality of auxiliary elastic members being attached in an extended condition to a location between the waist elastic members and the edge portions of the leg-encircling openings, said from and rear waist-encircling regions each comprising:

first elasticized zones which extend in the waist-encircling direction between each of the joined side edges of the front and rear waist-encircling regions and an adjacent side edge of the liquid absorbent core, said first elasticized zones having heights which extend in a longitudinal direction of the undergarment and a second elasticized zone which traverses a width of the liquid absorbent core and extends in the waist-encircling direction between opposite side edges of the liquid absorbent core, said second elasticized zone having a height which extends in the longitudinal direction of the undergarment, the first and second elasticized zones being adjacent to one another in the waist-encircling direction so that heights of ones of the first and second elasticized zones that are adjacent to one another in the waist-encircling direction are substantially coextensive along the waist-encircling direction and the first elasticized zones having a tensile stress that is greater than a tensile stress of the second elasticized zone, a tensile stress of the auxiliary elastic members is greater in the first elasticized zone than in the second elasticized zone.

2. A disposable pull-on undergarment which comprises:

a liquid pervious top sheet;

a liquid impervious back sheet;

a liquid absorbent core interposed between the top and back sheets;

front and rear waist-encircling regions opposed to each other and having longitudinal side edges that are joined together, at least one of said front and rear waist-encircling regions being elastically contractible in a waist-encircling direction;

a crotch region positioned between the front and rear waist-encircling regions;

a waist-encircling opening;

a pair of leg-encircling openings;

waist elastic members extending in the waist-encircling direction that are attached in an extended condition to an edge portion of the waist-encircling opening;

a plurality of first auxiliary elastic members spaced longitudinally apart from each other and extending in the waist-encircling direction in the first and second elasticized zones, which plurality of first auxiliary elastic members are attached in an extended condition to a location intermediate between the waist elastic members and the edge portions of the leg-encircling openings; and a plurality of second auxiliary elastic members spaced longitudinally apart from each other and extending in the waist-encircling direction in the first elasticized zone that are attached in an extended condition to a location intermediate between the waist elastic members and the edge portions of the leg-encircling openings, said front and rear waist-encircling regions each comprising:

first elasticized zones which extend in the waist-encircling direction between each of the joined side edges of the front and rear waist-encircling regions and an adjacent side edge of the liquid absorbent core, said first elasticized zones having heights which extend in a longitudinal direction of the undergarment and a second elasticized zone which traverses a width of the liquid absorbent core and extends in the waist-encircling direction between opposite side edges of the liquid absorbent core, said second elasticized zone having a height which extends in the longitudinal direction of the undergarment, the first and second elasticized zones being adjacent to one another in the waist-encircling direction so that heights of ones of the first and second elasticized zones that are adjacent to one another in the waist-encircling direction are substantially coextensive along the waist-encircling direction and the first elasticized zones having a tensile stress that is greater than a tensile stress of the second elasticized zone, a tensile stress of the first auxiliary elastic members being smaller than or equal to that of the second auxiliary elastic members.

3. The A disposable pull-on undergarment which comprises:

a liquid pervious top sheet;

a liquid impervious back sheet;

a liquid absorbent core interposed between the and back sheets;

front and rear waist-encircling regions opposed to each other and having longitudinal side edges that are joined together, at least one of said front and rear waist-encircling regions being elastically contractible in a waist-encircling direction;

a crotch region positioned between the front and rear waist-encircling regions;

a waist-encircling opening; and a pair of leg-encircling openings, said front and rear waist-encircling regions each comprising:

first elasticized zones which extend in the waist-encircling direction between each of the joined side edges of the front and rear waist-encircling regions and an adjacent side edge of the liquid absorbent core, said first elasticized zones having heights which extend in a longitudinal direction of the undergarment and a second elasticized zone which traverses a width of the liquid absorbent core and extends in the waist-encircling direction between opposite side edges of the liquid absorbent core, said second elasticized zone having a height which extends in the longitudinal direction of the undergarment, the first and second elasticized zones being adjacent to one another in the waist-encircling direction so that heights of ones of the first and second elasticized zones that are adjacent to one another in the waist-encircling direction are substantially coextensive along the waist-encircling direction, and the heights of all of the first and second elasticized zones is substantially equal throughout the front and rear waist-encircling regions, and the first elasticized zones having a tensile stress that is greater than a tensile stress of the second elasticized zone, said disposable pull-on undergarment further comprising:

waist elastic members extending in the waist-encircling direction are attached in an extended condition to an edge portion of the waist-encircling opening; and a plurality of auxiliary elastic members spaced longitudinally apart from each other and extending in the waist-encircling direction in the first and second elasticized zones, said plurality of auxiliary elastic members being attached in an extended condition to a location between the waist elastic members and the edge portions of the leg-encircling openings, a tensile stress of the auxiliary elastic members is greater in the first elasticized zone than in the second elasticized zone.

4. The A disposable pull-on undergarment which comprises:
- a liquid pervious top sheet;
- a liquid impervious back sheet;
- a liquid absorbent core interposed between the top and back sheets;
- front and rear waist-encircling regions opposed to each other and having longitudinal side edges that are joined together, at least one of said front and rear waist-encircling regions being elastically contractible in a waist-encircling direction;
- a crotch region positioned between the front and rear waist-encircling regions;
- a waist-encircling opening; and
- a pair of leg-encircling openings, said front and rear waist-encircling regions each comprising:
- first elasticized zones which extend in the waist-encircling direction between each of the joined side edges of the front and rear waist-encircling regions and an adjacent side edge of the liquid absorbent core said first elasticized zones having heights which extend in a longitudinal direction of the undergarment and
- a second elasticized zone which traverses a width of the liquid absorbent core and extends in the waist-encircling direction between opposite side edges of the liquid absorbent core, said second elasticized zone having a height which extends in the longitudinal direction of the undergarment,
- the first and second elasticized zones being adjacent to one another in the waist-encircling direction so that heights of ones of the first and second elasticized zones that are adjacent to one another in the waist-encircling direction are substantially coextensive along the waist-encircling direction, and the heights of all of the first and second elasticized zones is substantially equal throughout the front and rear waist-encircling regions, and the first elasticized zones having a tensile stress that is greater than a tensile stress of the second elasticized zone, said disposable pull-on undergarment further comprising:

waist elastic members extending in the waist-encircling direction that are attached in an extended condition to an edge portion of the waist-encircling opening;

a plurality of first auxiliary elastic members spaced longitudinally apart from each other and extending in the waist-encircling direction in the first and second elasticized zones, which plurality of first auxiliary elastic members are attached in an extended condition to a location intermediate between the waist elastic members and the edge portions of the leg-encircling openings; and a plurality of second auxiliary elastic members spaced longitudinally apart from each other and extending in the waist-encircling direction in the first elasticized zone that are attached in an extended condition to a location intermediate between the waist elastic members and the edge portions of the leg-encircling openings, a tensile stress of the first auxiliary elastic members being smaller than or equal to that of the second auxiliary elastic members.

* * * * *

UNITED STATES PATENT AND TRADEMARK OFFICE
CERTIFICATE OF CORRECTION

PATENT NO. : 7,331,946 B2 Page 1 of 1
APPLICATION NO. : 09/976182
DATED : February 19, 2008
INVENTOR(S) : Takaaki Shimada and Kenji Nakamura It is certified that error appears in the above-identified patent and that said Letters Patent is hereby corrected as shown below:

Column 9,
Line 14, should be changed from
"said from and rear waist-encircling regions each compris-"

to

-- said front and rear waist-encircling regions each compris- --

Column 10,
Line 21, should be changed from
"3. The A disposable pull-on undergarment which com-"

to

-- 3. A disposable pull-on undergarment which com- -- and

Column 11,
Line 19, should be changed from
"4. The A disposable pull-on undergarment which com-"

to

-- 4. A disposable pull-on undergarment which com- --

Signed and Sealed this

Twenty-first Day of October, 2008

JON W. DUDAS
*Director of the United States Patent and Trademark Office*